United States Patent
Benneker et al.

(10) Patent No.: US 7,601,245 B2
(45) Date of Patent: Oct. 13, 2009

(54) PROCESS FOR REDUCING THE ALDEHYDE CONCENTRATION IN A MIXTURE COMPRISING CYCLOHEXANONE AND ONE OR MORE ALDEHYDES

(75) Inventors: Arno H Benneker, Doenrade (NL); Augustinus P H Schouteten, Maastricht (NL); Larry W Wyatt, Augusta, GA (US)

(73) Assignee: DSM IP Assets B.V., Heerlen (NL)

( * ) Notice: Subject to any disclaimer, the term of this patent is extended or adjusted under 35 U.S.C. 154(b) by 632 days.

(21) Appl. No.: 10/540,229

(22) PCT Filed: Dec. 22, 2003

(86) PCT No.: PCT/NL03/00921

§ 371 (c)(1), (2), (4) Date: Oct. 5, 2005

(87) PCT Pub. No.: WO2004/058677

PCT Pub. Date: Jul. 15, 2004

(65) Prior Publication Data

US 2006/0124441 A1    Jun. 15, 2006

Related U.S. Application Data

(60) Provisional application No. 60/436,476, filed on Dec. 27, 2002.

(30) Foreign Application Priority Data

Mar. 19, 2003   (EP)   .................................. 03076125

(51) Int. Cl.
B01D 3/34 (2006.01)
C07C 45/82 (2006.01)

(52) U.S. Cl. .............................. 203/17; 203/36; 203/37; 203/79; 203/80; 564/502; 568/420

(58) Field of Classification Search .................. 203/17, 203/28, 36, 37, 79, 80; 568/342, 420; 564/502
See application file for complete search history.

(56) References Cited

U.S. PATENT DOCUMENTS

| 3,668,256 | A |   | 6/1972 | Brundege |
| 4,559,110 | A | * | 12/1985 | Swearingen et al. .......... 203/37 |
| 4,722,769 | A | * | 2/1988 | Chan et al. .................... 203/30 |
| 5,667,644 | A |   | 9/1997 | Mori et al. |
| 6,387,224 | B1 | * | 5/2002 | Pinkos et al. ................. 203/33 |
| 6,444,096 | B1 | * | 9/2002 | Barnicki et al. ............... 203/43 |

FOREIGN PATENT DOCUMENTS

| GB | 1 382 849 | 2/1975 |
| GB | 2 028 329 | 3/1980 |

* cited by examiner

*Primary Examiner*—Virginia Manoharan
(74) *Attorney, Agent, or Firm*—Nixon & Vanderhye P.C.

(57) ABSTRACT

The invention relates to a process for reducing the aldehyde concentration in a mixture comprising cyclohexanone and one or more aldehydes, said process comprising distilling said mixture in a distillation column in the presence of an alkaline compound, wherein in the bottom of the distillation column substantially no water is present.

26 Claims, No Drawings

PROCESS FOR REDUCING THE ALDEHYDE CONCENTRATION IN A MIXTURE COMPRISING CYCLOHEXANONE AND ONE OR MORE ALDEHYDES

This application is the US national phase of international application PCT/NL2003/000921 filed 22 Dec. 2003 which designated the U.S. and claims benefit of U.S. 60/436,476, dated 27 Dec. 2002 and EP 03076125.8, dated 19 Mar. 2003, the entire content of each of which is hereby incorporated by reference.

The invention relates to a process for reducing the aldehyde concentration in a mixture comprising cyclohexanone and one or more aldehydes.

Such a process is known from GB-A-2028329. This patent publication describes that aldehydes like caproaldehyde (hexanal) can be removed by subjecting a mixture comprising cyclohexanone and aldehydes to an aldol condensation reaction carried out in a separate aldol condensation vessel in the presence of an aqueous sodium hydroxide solution. The so-obtained mixture is subsequently washed with water to remove sodium hydroxide. In order to improve phase separation, cyclohexane is fed to the washing device. The washed organic mixture is subsequently distilled in a distillation column where low boiling components are distilled off.

A disadvantage of the process as described in GB-A-2028329 is that a separate aldol condensation reaction vessel and a washing device are needed. Another disadvantage is that in case the washing is effected in the presence of cyclohexane, cyclohexane has to be removed from the washed mixture.

The object of the present invention is to provide a simple and efficient process for removing aldehydes from cyclohexanone.

This object is achieved in that the process comprises distilling the mixture comprising cyclohexanone and one or more aldehydes in a distillation column in the presence of an alkaline compound, wherein in the bottom of the distillation column substantially no water is present.

Using the process of the invention cyclohexanone can be obtained having a purity with respect to aldehydes which is at least comparable to the purity of the cyclohexanone as obtained in the process as described in GB-A-2028329. Using the process of the present invention cyclohexanone having an increased purity with respect to aldehyde content can be obtained in a very simple manner. An advantage of the process of the invention is that a separate aldol-condensation reaction vessel and a washing device are not necessary. An additional advantage is that water and optionally cyclohexane which is/are added in the washing step does/do not have to be removed. This is advantageous because less process equipment is necessary and less energy is necessary to obtain cyclohexanone with sufficient purity with respect to aldehydes.

Aldehydes may for example be formed during the preparation of cyclohexanone. Examples of aldehydes are butanal, pentanal and hexanal. Said aldehydes include aldehydes which could hardly be separated from cyclohexanone under conventional distillation conditions. Aldehydes which could hardly be separated under conventional distillation conditions in particular concerns pentanal and hexanal. The presence of these aldehydes, and especially the presence of pentanal and hexanal, in cyclohexanone is undesired. In particular when cyclohexanone having a too high concentration of pentanal and hexanal (relative to the mixture comprising cyclohexanone, hexanal and/or pentanal) is processed into polycaprolactam (nylon-6) by oximation, Beckmann rearrangement and polymerization, the mechanical strength of the polycaprolactam obtained may be decreased to an undesired extent. When such cyclohexanone is processed into polycaprolactam, the aldehydes and especially pentanal and hexanal, even if present in low concentrations, give rise to impurities having a highly deleterious effect on the strength of the polycaprolactam. It has been found that the concentration of pentanal and hexanal in cyclohexanone is preferably lower than 90 weight ppm (relative to the mixture comprising cyclohexanone, pentanal and hexanal). The term weight ppm (parts per million) pentanal and hexanal is understood to mean the ratio of grams of the pentanal and hexanal per one million gram of the mixture comprising cyclohexanone, pentanal and/or hexanal.

In the process of the present invention, no or substantially no water is present in the bottom of the distillation column. As used herein, substantially no water means in particular that less than 100 weight ppm of water is present in the bottom of the distillation column (relative to the bottom product, i.e. the mixture present in the bottom of the distillation column contains less than 100 weight ppm of water). The term weight ppm (parts per million) water is understood to mean the ratio of grams of water per one million gram of bottom product. It has surprisingly been found that when the distilling is performed in the presence of less than 100 weight ppm of water in the bottom, the amount of aldehydes and in particular the amount of pentanal and hexanal can be decreased to very low values, even to below 90 weight ppm.

The presence of less than 100 weight ppm of water in the bottom of the distillation column can be obtained in any suitable way. Preferred methods are described in the present disclosure.

The process of the present invention is performed in a distillation column. The column may be any suitable distillation column. Examples of suitable distillation columns are tray columns or columns filled with a random or structured packing. The bottom of a distillation column is known to a person skilled in the art and refers in particular to the zone in which the liquid phase is present which is the most rich in high-boiling components, for example, the reboiler zone and the zone below the lowest tray for a tray distillation column and the reboiler zone and the zone below the packing for a distillation column filled with a packing.

The distillation may be carried out at any suitable temperature. The distillation is preferably carried out at a top temperature of between 45 and 130° C. and at a bottom temperature of between 105 and 190° C. The pressure applied at the top of the distillation column is in general between 0.02 and 0.15 MPa.

In the process of the invention, the mixture comprising cyclohexanone and aldehydes is distilled in the presence of an alkaline compound. Preferably, the mixture comprising cyclohexanone and aldehydes is distilled with an effective amount of alkaline compound to lower the concentration of pentanal and hexanal to such an extent that the concentration of pentanal and hexanal in the cyclohexanone is lower than 90 weight ppm.

Any suitable alkaline compound may be used. Suitable alkaline compounds include any alkaline compound capable of effecting aldol condensation of one or more of the aldehydes present in the mixture to be distilled, in particular of pentanal and hexanal. The alkaline compound is preferably an alkali metal compound. Preferred alkaline compounds are alkali metal hydroxide, alkali metal carbonates and alkali metal alkoxides. The alkali metal may be sodium, preferably potassium. In case an alkali metal compound is used, distilling the mixture comprising cyclohexanone and one or more aldehydes is preferably effected with such an amount of alkali metal compound that the concentration of alkali metal in the bottom of the distillation column is higher than 2 weight ppm and lower than 50 weight ppm. When more than 2 weight ppm of alkali metal is present in the bottom of the distillation column the amount of aldehydes and especially the amount of pentanal and hexanal in the cyclohexanone lowers to an increased extent. Using less than 50 weight ppm of alkali metal in the bottom of the distillation column is found to avoid or reduce loss of cyclohexanone.

The alkaline compound may be introduced in the mixture prior to feeding the mixture to the distillation column or it may be directly introduced to the distillation column. Preferably, the alkaline compound is introduced to the distillation column at the level where the mixture to be distilled in the distillation column is fed or in the zone below this level because this results in a decrease of cyclohexanone loss. The alkaline compound is preferably present in a mixture which is fed to the distillation column and more preferably in the mixture comprising cyclohexanone and one or more aldehydes to be distilled with the process of the present invention The alkaline compound may be fed to the distillation column in any suitable way, usually as a liquid. Preferably, the alkaline compound is fed to the distillation column by using a solution comprising water and the alkaline compound (hereinafter referred to as aqueous solution comprising the alkaline compound).

It has been found that in case an aqueous solution comprising the alkaline compound is used, said aqueous solution is advantageously fed to the distillation column at a level above the bottom of the distillation column. This is an advantage way to achieve that substantially no water is present in the bottom of the distillation column. In case a tray distillation column is used, said aqueous solution is advantageously fed to or above the first (numbered from the bottom of the distillation column to the top) tray of the distillation column. In case a packed distillation column is used, said aqueous solution is advantageously fed at a level where the packing is present.

Feeding the aqueous solution comprising the alkaline compound to the distillation column is preferably effected by feeding the aqueous solution comprising the alkaline compound directly to the distillation column at a level above the bottom of the distillation column and/or by feeding the aqueous solution comprising the alkaline compound to a mixture which is fed to the distillation column at a level above the bottom of the distillation column. The process according to the invention preferably comprises feeding the mixture comprising cyclohexanone and one or more aldehydes to the distillation column at a level above the bottom of the distillation column. The aqueous solution comprising the alkaline compound is preferably fed to the mixture comprising cyclohexanone and one or more aldehydes prior to feeding the mixture comprising cyclohexanone and one or more aldehydes at a level above the bottom of the distillation column.

Particularly suitable aqueous solutions are aqueous solutions of alkali metal hydroxides, alkali metal carbonates, alkali metal alkoxides in particular alkali metal cyclohexanolate. When the aqueous solution is fed directly to the distillation column or when the aqueous solution is fed to the mixture comprising cyclohexanone and one or more aldehydes, the aqueous solution preferably contains from 0.5 to 50 wt. %, more in particular from 5 to 45 wt. % of the alkali metal compound, preferably of sodium hydroxide, most preferably of potassium hydroxide.

In particular, the amount of aqueous potassium hydroxide solution directly introduced in the distillation column or in the mixture prior to feeding the mixture to the distillation column is preferably such that at least 2 weight ppm and more preferably at least 5 weight ppm of potassium is present in the bottom of the distillation column because by using less than 2 weight ppm of potassium in the bottom of the distillation column the amount of aldehydes and especially the amount of pentanal and hexanal in the cyclohexanone lowers to a lesser extent. The amount of aqueous solution of potassium hydroxide introduced into the distillation column is preferably such that that the amount of potassium in the bottom of the distillation column is not higher than 50 weight ppm and more preferably not higher than 40 weight ppm and even more preferred not higher than 35 weight ppm because it has been found that the use of more than 35 weight ppm of potassium in the bottom of the distillation column results in an increased loss of cyclohexanone.

The mixture comprising cyclohexanone and one or more aldehydes which is distilled in the process of the invention can be obtained with various known processes. The mixture usually comprises more than 200 weight ppm of aldehydes and less than 6000 weight ppm of aldehydes (relative to the mixture). The mixture usually comprises more than 500 weight ppm and less than 5000 weight ppm pentanal and hexanal (relative to the mixture).

Preparing of the mixture, for example, involves oxidizing cyclohexane in the liquid phase with an oxygen containing gas in the presence or absence of an oxidation catalyst. In one embodiment of the invention, preparing the mixture involves oxidizing cyclohexane in the presence of an oxidation catalyst resulting in an oxidized mixture comprising cyclohexane, cyclohexanone and cyclohexanol, and typically also low and high boiling compounds.

In another and preferred embodiment of the invention, preparing the mixture involves oxidizing cyclohexane in the absence of an oxidation catalyst resulting in an oxidation mixture comprising cyclohexane, cyclohexyl hydroperoxide, cyclohexanone and cyclohexanol and subsequently treating this mixture with a cyclohexyl hydroperoxide-decomposing metal salt in the presence of an aqueous solution of an alkali metal hydroxide to effect decomposition of the cyclohexyl hydroperoxide into cyclohexanone and cyclohexanol to obtain a mixture comprising cyclohexane, cyclohexanone, cyclohexanol, and typically also low boiling and high boiling components. In one embodiment, the mixture comprising cyclohexane, cyclohexanone and cyclohexanol is distilled in the presence of an alkaline compound according to the invention. In another and more preferred embodiment, preparing of the mixture further involves separating cyclohexane from the mixture comprising cyclohexane, cyclohexanone and cyclohexanol to obtain the mixture to be distilled in the presence of an alkaline compound according to the invention. The process of the present invention therefore also relates to a process comprising oxidizing cyclohexane in the liquid phase with an oxygen containing gas, resulting in an oxidation mixture comprising cyclohexane, cyclohexyl hydroperoxide, cyclohexanone and cyclohexanol; treating the oxidation mixture with a cyclohexyl hydroperoxide decomposing metal salt in the presence of an alkali metal hydroxide such as to effect decomposition of the cyclohexyl hydroperoxide into cyclohexanone and cyclohexanol, resulting in a mixture comprising cyclohexanone, cyclohexanol and cyclohexane; separating, by distillation, cyclohexane from the mixture comprising cyclohexanone, cyclohexanol and cyclohexane; separating, by distillation, low boiling compounds from the resulting mixture to obtain a top product comprising low boiling compounds and a bottom product comprising cyclohexanone, cyclohexanol and high boiling compounds; and effecting the distillation to separate cyclohexane or the distillation to separate low boiling compounds in the presence of an alkaline compound in a distillation column, wherein in the bottom of the distillation column substantially no water is present. This specific combination of steps was found to result in cyclohexanone having an extremely low concentration of aldehydes, in particular of pentanal and hexanal, without having to use a separate aldol condensation step and washing step. With low boiling compounds is meant compounds having a boiling point lower than cyclohexanone and higher than cyclohexane. Examples are butanol, pentanal, hexanal, pentanol and epoxy cyclohexane. With high boiling compounds is meant compounds having a boiling point higher than cyclohexanol. Examples are 2-cyclohexylidene cyclohexanone, 2-hexylidene cyclohexanone and 2-(cyclohexen-1-yl)cyclohexanone. In EP-A-579323 an exemplary process is described for oxidizing cyclohexane in the absence of an oxidation catalyst resulting in an oxidation mixture comprising cyclohexane, cyclohexyl hydroperoxide, cyclohexanone and cyclohexanol. In GB-A-1382849 and EP-A-4105 exemplary processes are described for treating a mixture comprising cyclohexane, cyclohexyl hydroperoxide, cyclohexanone and cyclohexanol with a cyclohexyl hydroperoxide-decomposing metal salt in the presence of an aqueous solution of an alkali metal hydroxide to effect decomposition of the cyclohexyl hydroperoxide into cyclohexanone and cyclohexanol.

The oxidized mixture or mixture obtained after decomposition is usually processed by first distilling off cyclohexane and the by-products that are more volatile than the cyclohexane, followed by distilling off low boiling compounds, subsequently cyclohexanone and finally the cyclohexanol. Cyclohexanol may subsequently subjected to a dehydrogenation reaction using a dehydrogenator. In one embodiment of the invention, the process of the present invention is performed in a distillation column in which cyclohexane is distilled off. Preferably, the process of the present invention is performed in a distillation column in which low boiling components are separated from a mixture also containing cyclohexanone, cyclohexanol, and high boiling compounds to obtain a top product comprising low boiling compounds and a bottom product comprising cyclohexanone, cyclohexanol and high boiling compounds. A preferred embodiment of the present invention therefore relates to a process to distill off low boiling components from a mixture also comprising cyclohexanone, cyclohexanol and high boiling compounds, said mixture also including hexanal and/or pentanal, in the presence of an alkaline compound in a distillation column in which in the bottom no or substantially no water is present. Usually, the mixture which is fed to the distillation column in which low boiling components are distilled off, comprises between 40 and 60 wt. % cyclohexanone, between 40 and 60 wt. % cyclohexanol, typically between 0.2 and 2 wt. % low-boiling compounds and typically between 1 and 4 wt. % high boiling compounds and typically between 200 and 6000 weight parts per million of aldehydes, in particular 500-5000 weigth ppm hexanal and pentanal.

The process of the invention will now be further elucidated with the following non-limiting examples.

Experiment A

A mixture, comprising cyclohexanone, cyclohexanol and low and heavy boiling compounds was fed to a first distillation column at a rate of 25 m³/hr. Pentanal and hexanal concentrations in the mixture were 70 and 300 weight ppm respectively. The mixture was fed to the 23$^{rd}$ tray of the total 60 sieve trays (trays numbered from bottom to top). The column was operated at 0.08 MPa and 121° C. at the top of the column and about 0.1 MPa at tray with number 20 and 165° C. at the bottom of the column. 14 t/h steam (1.25 MPa) was applied in the reboiler. Low boiling products, such as n-butanol, n-pentanol, hexanal and epoxy cyclohexane were separated off via the top of the column. An aqueous solution of 5 wt % KOH was added to the bottom of the distillation column at a rate of 50 ml/min, resulting in a water concentration of 150 weight ppm and a potassium concentration of 5 weight ppm in the bottom product. The bottom product was withdrawn from the distillation column and mixed with a 25 m³/hr mixture of cyclohexanone, cyclohexanol and heavy boiling components. This mixture was fed to the top of a second distillation column. The second column is a packed column and operates at approximately 74° C. at the top of the column; and 10.7 kPa at 103° C. at the bottom of the column. Cyclohexanol and heavy boiling components left the bottom of the second distillation column. The pentanal and hexanal concentrations in the top product (mainly comprising cyclohexanone) were 12 and 130 weight ppm respectively Concentration of CHIA (2-cyclohexylidene cyclohexanone which is a dimer of cyclohexanone) in the bottom of the first distillation column was 0.1 wt. %, indicating that product losses due to dimerization of cyclohexanone were small.

Comparative Experiment B

Experiment A was repeated with the difference that pentanal and hexanal concentrations in the feed of the first distillation column were 400 weight ppm and 2100 weight ppm. No aqueous KOH solution was fed to the first distillation column. The pentanal and hexanal concentrations in the top product (mainly comprising cyclohexanone) of the second column were 20 and 190 weight ppm respectively (relative to the cyclohexanone present in the top product). Concentration of CHIA (2-cyclohexylidene cyclohexanone) in the bottom of the first distillation column was 0.1 wt. %, indicating that product losses due to dimerization of cyclohexanone were small.

Experiment C

A mixture of cyclohexanone, cyclohexanol, low and heavy boiling compounds, 400 weight ppm pentanal and 2100 weight ppm hexanal, was treated with 2.5 m³/hr NaOH solution, having an alkalinity of 2 meq/g, in a stirred saponification vessel at a rate of 25 m³/hr at 103° C. during 15 minutes. The resulting mixture was mixed with 20 m³/hr cyclohexane and sent to a separation vessel to separate the aqueous phase. The organic mixture was countercurrently washed in a packed column with 7 m³/hr water to extract the water droplets containing sodium. The washed organic mixture was sent to the top of a drying column to remove cyclohexane and water. The drying column had 15 sieve trays and was operated at a pressure of about 0.1 MPa, a top temperature of about 78° C., and a bottom temperature of about 161° C. Pentanal and hexanal concentrations in the bottom product of the drying column were 70 and 300 ppm. Comparative Experiment B was repeated with this bottom product as feedstock, resulting in pentanal and hexanal concentrations in the top product of the second column of 6 and 60 weight ppm respectively (relative to the cyclohexanone present in the top product). Concentration of CHIA (2-cyclohexylidene cyclohexanone) in the bottom of the first distillation column was 0.1 wt. %, indicating that product losses due to dimerization of cyclohexanone were small.

EXAMPLE I

Experiment A was repeated with the difference that the 50 ml/min 5 wt. % KOH solution was fed in the feed pipe of the first distillation column. Potassium concentration in the bottom was 5 weigth ppm (hereinafter referred to as ppmw) and the water concentration in the bottom was <10 ppmw. The pentanal and hexanal concentrations in the top product of the second column were 4 and 50 ppmw respectively (relative to the cyclohexanone present in the top product). Concentration of CHIA (2-cyclohexylidene cyclohexanone) in the bottom of the first distillation column was 0.07 w %.

Comparison of Example I with Experiment C indicates that with the process of the invention cyclohexanone with an even increased purity with respect to pentanal and hexanal can be obtained in a very simple manner.

EXAMPLE II

Example I was repeated with the difference that the KOH solution flow rate was increased to 70 ml/min. Potassium concentration in the botttom was 7 ppmw and water concentration in the bottom was <10 ppmw. The pentanal and hexanal concentrations in the top product of the second column were 2 and 15 ppmw respectively (relative to the cyclohexanone present in the top product). Concentration of CHIA (2-cyclohexylidene cyclohexanone) in the bottom of the first distillation column was 0.10 wt %.

Example III

Example I was repeated with the difference that the KOH solution flow rate was increased to 350 ml/min. Potassium concentration in the bottom was 35 ppmw and water concentration in the bottom was <10 ppmw. The pentanal and hexanal concentrations in the top product of the second column were 1 and 5 ppmw respectively (relative to the cyclohexanone present in the top product). Concentration of CHIA (2-cyclohexylidene cyclohexanone) in the bottom of the first distillation column was 0.35 wt %.

The invention claimed is:

1. Process for reducing the aldehyde concentration in a mixture comprising cyclohexanone and one or more aldehydes comprising:
   oxidizing cyclohexane in a liquid phase with an oxygen containing gas resulting in an oxidation mixture comprising cyclohexane, cyclohexyl hydroperoxide, cyclohexanone and cyclohexanol;
   treating the oxidation mixture with a cyclohexyl hydroperoxide decomposing metal salt in the presence of an alkali metal hydroxide such as to effect decomposition of the cyclohexyl hydroperoxide into cyclohexanone and cyclohexanol, resulting in a mixture comprising cyclohexanone, cyclohexanol and cyclohexane;
   separating, by a first distillation, cyclohexane from the mixture comprising cyclohexanone, cyclohexanol and cyclohexane to thereby obtain a resulting mixture comprising cyclohexanone and cyclohexanol; and
   separating, by a second distillation, low boiling compounds from the resulting mixture comprising cyclohexanone and cyclohexanol to obtain a top product comprising low boiling compounds and a bottom product comprising cyclohexanone, cyclohexanol and high boiling compounds; wherein
   the process further comprises reducing the aldehyde concentration in the mixture comprising cyclohexanone and one or more aldehydes by carrying out at least one of the first and second distillations in a distillation column in the presence of an alkaline compound, wherein less than 100 weight ppm of water is present in the bottom of the distillation column.

2. Process according to claim 1, wherein the process further comprises feeding said bottom product to another distillation column in which cyclohexanone is distilled off as a top product.

3. Process according to claim 1, wherein the resulting mixture from the first distillation comprises cyclohexanone, cyclohexanol, low boiling compounds and high boiling compounds and wherein the distilling in the second distillation involves separation of low boiling compounds to obtain a top product comprising low boiling compounds and a bottom product comprising cyclohexanone, cyclohexanol and high boiling compounds.

4. Process according to claim 1, wherein the aldehydes are hexanal and/or pentanal.

5. Process according to claim 1, wherein the second distillation column is operated at a top temperature of between 45 and 130° C. and a bottom temperature of between 105 and 190° C.

6. Process according to claim 1, wherein the process comprises feeding a solution comprising water and the alkaline compound to the distillation column at a level above the bottom of the distillation column.

7. Process according to claim 1, wherein the process comprises feeding the mixture resulting from the decomposition treatment of the liquid phase cyclohexane oxidation to said distillation column and feeding a solution comprising water and the alkaline compound to the distillation column at a level above the bottom of the distillation column.

8. Process according to claim 1, wherein the process comprises feeding the mixture to the distillation column at a level above the bottom of the distillation column and introducing a solution comprising water and the alkaline compound into the mixture prior to said feeding.

9. Process according to claim 1, wherein the alkaline compound is an alkali metal compound.

10. Process according to claim 9, wherein the distillation column is operated with an amount of alkali metal compound such that the concentration of alkali metal in the bottom of the distillation column is higher than 2 weight ppm and lower than 50 weight ppm.

11. Process according to claim 1, wherein the alkaline compound is an alkali metal hydroxide, alkali metal carbonate or alkali metal alkoxide.

12. Process according to claim 1, wherein the alkaline compound is sodium hydroxide or potassium hydroxide.

13. Process according to claim 1, which further comprises feeding the bottom product of the second distillation to a distillation column in which cyclohexanone is distilled off as a top product.

14. Process for reducing the aldehyde concentration in a mixture comprising cyclohexanone and one or more aldehydes, the process comprising:
   oxidizing cyclohexane in a liquid phase with an oxygen containing gas in the absence of an oxidation catalyst resulting in an oxidation mixture comprising cyclohexane, cyclohexyl hydroperoxide, cyclohexanone and cyclohexanol;
   treating the oxidation mixture with a cyclohexyl hydroperoxide decomposing metal salt in the presence of an alkali metal hydroxide such as to effect decomposition of the cyclohexyl hydroperoxide into cyclohexanone and cyclohexanol to obtain a mixture comprising cyclohexanone and one or more aldehydes; and
   reducing the aldehyde concentration in the mixture by distilling the mixture in a distillation column in the presence of an alkaline compound, wherein less than 100 weight ppm of water is present in the bottom of the distillation column.

15. Process according to claim 14, further comprising separating cyclohexane from the mixture prior to distilling.

16. Process according to claim 14, wherein the mixture resulting from the decomposition treatment of the liquid phase cyclohexane oxidation comprises cyclohexanone, cyclohexanol, low boiling compounds and high boiling compounds and wherein said distilling involves separation of low boiling compounds to obtain a top product comprising low boiling compounds and a bottom product comprising cyclohexanone, cyclohexanol and high boiling compounds.

17. Process according to claim 14, wherein the aldehydes are hexanal and/or pentanal.

18. Process according to claim 14, wherein the distillation column is operated at a top temperature of between 45 and 130° C. and a bottom temperature of between 105 and 190° C.

19. Process according to claim 14, wherein the process comprises feeding a solution comprising water and the alkaline compound to the distillation column at a level above the bottom of the distillation column.

20. Process according to claim 14, wherein the process comprises feeding the mixture resulting from the decomposition treatment of the liquid phase cyclohexane oxidation to said distillation column and feeding a solution comprising water and the alkaline compound to the distillation column at a level above the bottom of the distillation column.

21. Process according to claim 14, wherein the process comprises feeding the mixture to the distillation column at a level above the bottom of the distillation column and introducing a solution comprising water and the alkaline compound into the mixture prior to said feeding.

22. Process according to claim 14, wherein the alkaline compound is an alkali metal compound.

23. Process according to claim 22, wherein the distillation column is operated with an amount of alkali metal compound such that the concentration of alkali metal in the bottom of the distillation column is higher than 2 weight ppm and lower than 50 weight ppm.

24. Process according to claim 14, wherein the alkaline compound is an alkali metal hydroxide, alkali metal carbonate or alkali metal alkoxide.

25. Process according to claim 14, wherein the alkaline compound is sodium hydroxide or potassium hydroxide.

26. Process according to claim 14, which further comprises feeding the bottom product to a distillation column in which cyclohexanone is distilled off as a top product.

* * * * *